(12) United States Patent
Sieveking et al.

(10) Patent No.: US 9,572,817 B2
(45) Date of Patent: Feb. 21, 2017

(54) USE OF ANDROGENS FOR VASCULAR REGENERATION AND ENDOTHELIAL REPAIR

(75) Inventors: Daniel Peter Sieveking, Summer Hill (AU); Martin Kean Chong Ng, Mosman (AU)

(73) Assignee: THE HEART RESEARCH INSTITUTE LTD., Newtown (AU)

( * ) Notice: Subject to any disclaimer, the term of this patent is extended or adjusted under 35 U.S.C. 154(b) by 961 days.

(21) Appl. No.: 13/002,382

(22) PCT Filed: Jul. 4, 2008

(86) PCT No.: PCT/AU2008/000993
§ 371 (c)(1),
(2), (4) Date: Oct. 17, 2011

(87) PCT Pub. No.: WO2010/000011
PCT Pub. Date: Jan. 7, 2010

(65) Prior Publication Data
US 2012/0039851 A1 Feb. 16, 2012

(51) Int. Cl.
*A61K 31/56* (2006.01)
*A61K 31/568* (2006.01)
*A61K 31/5685* (2006.01)

(52) U.S. Cl.
CPC ............. *A61K 31/56* (2013.01); *A61K 31/568* (2013.01); *A61K 31/5685* (2013.01)

(58) Field of Classification Search
CPC ... A61K 31/56; A61K 31/568; A61K 31/5685
See application file for complete search history.

(56) References Cited

U.S. PATENT DOCUMENTS

| 6,017,924 | A * | 1/2000 | Edwards et al. | ............... | 514/292 |
| 6,583,129 | B1 * | 6/2003 | Mazer et al. | ................. | 514/167 |
| 2002/0065273 | A1 | 5/2002 | Chein | | |
| 2003/0199464 | A1 | 10/2003 | Itescu | | |
| 2005/0233992 | A1 | 10/2005 | Itescu | | |

FOREIGN PATENT DOCUMENTS

| EP | 1210951 B1 | 2/2005 |
| WO | WO 03/020329 A1 | 3/2003 |
| WO | WO 2006/078853 A2 | 7/2006 |
| WO | WO 2007/035451 A2 | 3/2007 |
| WO | WO 2007/149548 A2 | 12/2007 |

OTHER PUBLICATIONS

Rosano et al. Acute Anti-Ischemic Effect of Testosterone in Men With Coronary Artery Disease. Circulation. 1999;99:1666-1670.*
Webb et al. Effects of Testosterone on Coronary Vasomotor Regulation in Men With Coronary Heart Disease. Circulation. 1999;100:1690-1696.*
Zampetaki et al. Vascular repair by endothelial progenitor cells. Cardiovascular Research (2008) 78, 413-421.*
Ray et al. Sex Steroids and Stem Cell Function. Mol. Med. (2008) 14 (7-8):493-501.*
Kawamoto et al. Therapeutic Potential of Ex Vivo Expanded Endothelial Progenitor Cells for Myocardial Ischemia. Circulation. 2001;103:634-637.*
Foresta et al. Androgens stimulate endothelial progenitor cells through an androgen receptor-mediated pathway. Clinical Endocrinology (2008) 68, 284-289.*
Zhao et al. Autologous endothelial progenitor cells transplantation promoting endothelial recovery in mice. Transplant International 20 (2007) 712-721.*
Kang et al. Effect of Oral Administration of Testosterone on Brachial Arterial Vasoreactivity in Men With Coronary Artery Disease. The American Journal of Cardiology vol. 89 Apr. 1, 2002. 869-864.*
Englsih et al. Low-Dose Transdermal Testosterone Therapy Improves Angina Threshold in Men With Chronic Stable Angina A Randomized, Double-Blind, Placebo-Controlled Study. Circulation. 2000;102:1906-1911.*
Mulligan et al.Prevalence of hypogonadism in males aged at least 45 years: the HIM study. Int J Clin Pract, Jul. 2006, 60, 7, 762-769.*
Buckle et al., "Hyperglycaemia Inhibits Thioredoxin-Medicated Angiogenesis: Implications for Impairment of Neovascularisation in Diabetes Mellitus," Heart, Lung and Circulation, Elsevier, 2007, pp. S211-S217, vol. 16.
Chu, K. et al., "Circulating Endothelial Progenitor Cells as a New Marker of endothelial Dysfunction or Repair in Acute Stroke," Stroke, 2008, pp. 1441-1447, vol. 39.
Dunn, L. et al, "Gene Silencing of Thioredoxin Interacting Protein Dramatically Rescues Diabetes-Related Impairment of Angiogenesis in Vitro and in Vivo," Heart, Lung and Circulation, Elsevier, 2009, pp. S243, vol. 18.
Dunn, L. et al., "Rescue of Diabetes-Related Impairment of Angiogenesis by Gene Silencing of Thioredoxin-Interacting Protein," Heat Lung and Circulation, Elsevier, 2008, S3-S4, vol. 17.
Dunn, L. et al., "Type 1 Diabetes Mellitus is Associated with Impairment of Late Outgrowth Endothelial Progenitor Cell Function," Heart, Lung and Circulation, Elsevier, 2008, pp. S138, vol. 17.
Marumo, T. et al., "Aldosterone Impairs Bone Marrow-Derived Progenitor Cell Formation," Hypertension, 2006, pp. 490-496, vol. 48.

(Continued)

*Primary Examiner* — Taeyoon Kim
(74) *Attorney, Agent, or Firm* — Fenwick & West LLP

(57) ABSTRACT

The present invention relates to the field of therapy and prophylaxis of vascular tissue damage and/or complications and/or disease of vascular tissue by vascular regeneration and endothelium repair. The inventors have found that administration of an androgen receptor agonist alleviates one or more adverse vascular diseases and/or vascular complications thereof or adverse effects of androgen deficiency, with implications for prophylactic and therapeutic interventions.

15 Claims, 12 Drawing Sheets

(56) References Cited

OTHER PUBLICATIONS

PCT International Search Report and Written Opinion, PCT Application No. PCT/AU2008/000993, Aug. 14, 2009, 9 pages.
Schulze, P.C. et al., "Hyperglycemia Promotes Oxidative Stress Through Inhibition of Thioredoxin Function by Thiordexin-Interacting Protein," Journal of Biological Chemistry, 2004, pp. 30369-30374, vol. 279, No. 29.
Werner, G.S. et al., "Direct Assessment of Coronary Steal and Associated Changes of Collateral Hemodynamics in Chronic Total Coronary Occlusions," Circulation, Jul. 23, 2002, pp. 435-440, vol. 106.

\* cited by examiner

USE OF ANDROGENS FOR VASCULAR REGENERATION AND ENDOTHELIAL REPAIR

FIELD OF THE INVENTION

The present invention relates to the field of therapy and prophylaxis of vascular tissue damage and/or complications and/or disease of vascular tissue by vascular regeneration and endothelial repair.

BACKGROUND OF THE INVENTION

Angiogenesis/Vasculogenesis

Angiogenesis and vasculogenesis are important processes in animal development. A large body of evidence indicates that angiogenesis and vasculogenesis play a critical role in physiological processes such as wound healing and tissue vascularisation in response to injury and ischaemia, and the enhancement of collateral circulation. The development of coronary collateral circulation in response to coronary ischaemia ameliorates adverse outcomes of ischemic heart disease, such as acute myocardial infarction, angina and heart failure. Myocardial viability after acute myocardial infarction correlates with the extent of collateral blood flow with the affected vascular segment. Therapeutic neovascularisation is therefore considered as a very promising approach to prevent the serious clinical consequences (heart failure, gangrene, neuronal disability) of abnormal tissue remodelling in patients suffering from cardiovascular ischemic disease.

The mechanisms for ischaemia-induced collateral formation, however, are poorly understood.

Heart Failure

Heart failure, characterized by a severe deficiency in ventricular pump function, is a major public health problem. It arises through a number of intrinsic factors and extrinsic factors. An example of one such extrinsic factor includes myocyte loss that is unmatched by myocyte replacement, frequently the end result of cardiovascular disease. Replacement and/or regeneration of functional cardiac muscle after an ischemic insult to the heart is thought possible by stimulating proliferation of endogenous mature cardiomyocytes or resident cardiac stem cells, by implanting exogenous donor-derived or allogeneic cells, or by supplementing the angiogenic mechanisms that occur naturally using defined growth factors or vessel forming cells (Dimmeler, S. et al "Unchain my heart: the scientific foundations of cardiac repair" *J Clin Invest.* Vol. 115, No. 3, 2005; and Orlic, D. et al "Mobilized bone marrow cells repair the infarcted heart, improving function and survival", *Proc Natl Acad Sci USA.* Vol. 98, No. 18, 2001).

In addition to the heart, other end-organ targets of cardiovascular disease include the kidney and the brain. The endothelial layer is a key regulator of blood flow to these organs. As such, maintenance of the endothelium is thought necessary for the prevention of end-organ effects such as kidney disease and stroke.

Coronary Artery Disease and Ischemic Heart Disease

The disease process underlying most ischemic heart disease is atherosclerosis of the coronary arteries (coronary heart disease). Atherosclerosis is a disease whereby plaque builds up on the inside of arteries. This fatty material thickens, hardens and may eventually block the artery. This makes it harder for blood to flow. If the coronary arteries become narrow, blood flow to the heart can slow down or stop, causing chest pain, shortness of breath, heart attack, and other symptoms.

Recent clinical research has included investigation of the therapeutic benefit of mobilising endothelial progenitor cells (EPCs). Hill et al., "Outcomes and Risks of Granulocyte Colony-Stimulating Factor in Patients with Coronary Heart Disease", *Journal of the American College of Cardiology*, Vol. 46, No. 9 (2005) investigated vascular progenitor cells for the potential for cardiovascular repair following injury. Hill et al., found that although investigators using the hind-limb ischaemia model and carotid injury model and a small clinical trial had suggested favourable effects of a cytokine mobilization approach, no progenitor cell mobilization was observed. Hill et al., concluded that administration of granulocyte colony-stimulating factor to CAD patients mobilizes CD34+/CD133+ progenitor cells into the circulation, however no objective evidence was obtained that there was any cardiac benefit.

Further research in the area of angiogenesis and cardiovascular regeneration is essential to the treatment of ischemic heart disease. With economic development and the associated decline in communicable diseases globally, cardiovascular disease and in particular ischemic heart disease is now the leading cause of mortality worldwide and is expected to remain so well into the twenty first century.

Coronary Vascular Surgery

Both surgical revascularization (coronary artery bypass grafting) and percutaneous coronary intervention (PCI) are established treatment options for coronary heart disease. However, a major drawback of PCI is damage to the endothelium caused by the stent.

Expansion of a stent in a target artery induces local injury of the vessel wall, primarily from the disruption of the endothelial lining (the endothelium is a layer of flat cells lining the closed internal spaces of the body such as the inside of blood vessels and lymphatic vessels and the heart). Following the injury, the reparatory mechanisms are activated leading to recovery of the endothelial coverage over the stent struts.

Disruption of the endothelium causes the activation and adherence of platelets and recruitment of the monocytes and leukocytes. The time that elapses between the endothelial disruption caused by the expanded stent and full coverage of the struts with new endothelial cells carries the highest risk of in-stent thrombosis. At the same time the initial events of in-stent restenosis also occur, primarily migration and proliferation of smooth muscle cells. The key event in rebuilding the endothelial layer over the stent struts is the recruitment of circulating endothelial progenitor cells (EPC), their adherence and attachment to the surface of the stent and vascular wall between the struts. The full coverage of the prothrombotic metal struts with new endothelial cells reduces the initially high risk of thrombosis.

Limb Ischaemia

Critical limb ischaemia, the most severe form of peripheral vascular disease, leads to over 160,000 major limb amputations per year. Therapeutic options are limited and largely ineffective for the most severe patients. Vascular regeneration is one potential option to repair and regenerate the ischemic tissues of these patients to improve the blood flow in the affected areas.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

1. Background

In work leading to the present invention, the inventors sought to investigate the role of androgens (and their withdrawal) in the maintenance of vascular homeostatic and regenerative processes. The inventors sought to investigate the role of androgens in vascular disease and injury and in particular on the cardiovascular response to ischaemia and vascular injury.

The inventors made the following hypothesis:
(i) androgens have an effect on the rate and extent of vascular regeneration including neovascularisation and angiogenesis,
(ii) androgens effect the rate and extent of endothelial progenitor cell (EPC) mobilisation and function, and
(iii) there are gender dependent differences in the androgenic regulation of vascular genesis.

The inventors hypothesised that their findings would have implications for understanding of the repair of the vascular system and its end organs (such as for example the heart or kidneys) in response to aging, disease and injury and in particular the repair and regeneration of the cardiovascular system.

The inventors hypothesised that their findings would have important implications for understanding of vascular effects of the age-related decline in circulating androgens and gender differences in outcomes following coronary disease or complications as a result thereof.

The inventors further hypothesised that their findings would have important implications for understanding of androgen deficiency and androgen therapy particularly older subjects. The inventors theorized that knowledge of the androgen effects on vascular regeneration and EPC function will provide a better understanding of gender differences in vascular diseases and vascular injury and will guide efforts to exploit the wider therapeutic benefit of androgens in vascular therapies.

As used herein the terms to "promote vascular repair" or "enhance vascular repair" shall be construed in their broadest context to include the initiation or enhancement or improvement of any process that enhances the ability of a cell to contribute to vascular repair and/or induces, initiates, derepresses or otherwise enhances vascular repair for example by augmenting a cells capacity for vascular repair and/or angiogenesis and/or neovascularisation.

As used herein, the term "angiogenesis" shall be taken to mean a process by which new blood vessels are formed whether from extant blood vessels or not and/or the enlargement of pre-existing blood vessels.

As used herein, the term "neovascularization" shall be taken to mean a development of new blood vessels in tissues not possessing extant blood vessels. Neovascularization in adults is thought to be a mixed phenomenon of angiogenesis and vasculogenesis. Vasculogenesis is understood to be the differentiation of endothelial progenitor cells or stem cells or cells capable of adopting an endothelial lineage to endothelial cells (ECs) and subsequent formation of primary vascular plexus.

Angiogenesis and neovascularisation are understood to be important processes of vascular regeneration and may collectively or alternatively be referred to herein as vascular regeneration. As used herein vascular regeneration is to be understood in its broadest sense to also include other repair processes including endothelial cell migration, proliferation and mobilisation.

The term "endothelial progenitor cell" or "EPC" shall be construed in its broadest context to mean a cell that, when functional or normal, is capable of proliferating to form blood vessels e.g., in the formation of a vascular network or in vascular repair, such as by angiogenesis and/or neovascularisation. EPCs may be functional, non-functional, or have impaired function (for example with respect to this proliferative ability and developmental capability), and non-functional EPCS or EPCs having impaired function may be identified readily (for example by their aberrant morphology and impaired proliferative ability).

The term "endothelial cell" or "EC" as used herein is to be construed in its broadest sense to refer to a cell capable of forming the endothelium. EPCs are understood t have an ability to differentiate into endothelial cells.

The inventors studied the effects of androgens on three key vascular repair (angiogenic) processes: vascular tubulogenesis, endothelial cell migration, and endothelial cell proliferation. The investigations were conducted in both in vitro and in vivo settings.

In summary, the present inventors have demonstrated that androgens promote angiogenesis and neovascularisation processes and this has important implications for subjects with impaired vascular function or vascular disease and/or vascular complications thereof, and that administration of an androgen has utility in preventing one or more vascular diseases and/or vascular complications thereof from arising or developing and/or reducing the severity of vascular diseases and/or vascular complications thereof and/or enhancing vascular repair e.g., by promoting, inducing or enhancing vascular repair through tubulogenesis, angiogenesis and neovascularisation processes.

As exemplified herein, the inventors have shown that in vitro androgen administration induced dose-dependent male EC migration and a dose-related increase in EC proliferation. Chronic exposure to androgens also increased tubule formation.

As exemplified herein, the inventors demonstrated in vivo that male castration markedly decreased in vivo vascularisation processes and furthermore that androgen replacement reversed castration-effects on angiogenesis.

As exemplified herein, the inventors demonstrated in vivo that male castration markedly inhibited the rate of recovery from hind limb ischaemia. Androgen replacement not only reversed castration-effects, but also accelerated recovery in hind limb ischaemia. These results were also mirrored in clinical evaluations of ischemic damage and motor function.

These findings suggest that repair and/or regeneration of damaged (or aged) endothelium can be augmented by androgens. These findings support the hypothesis that androgens participate in promotion of vascular repair and has particular implications for cardiovascular regeneration and the role of androgen replacement in subjects deficient of androgens, especially men.

Taken together, these findings by the inventors have indicated that administration of an androgen receptor agonist alleviates one or more adverse vascular diseases and/or vascular complications thereof or adverse effects of androgen deficiency, with implications for prophylactic and therapeutic interventions.

2. Specific Embodiments

The scope of the invention will be apparent from the claims as filed with the application that follow the examples.

The claims as filed with the application are hereby incorporated into the description. The scope of the invention will also be apparent from the following description of specific embodiments.

The present invention relates to methods of therapy which promote vascular repair and regeneration. The present invention also provides a use of an androgen receptor agonist in the preparation of a medicament for conditions which benefit from promoting vascular repair and regeneration.

The methods are particularly useful for example:
to promote angiogenesis and neovascularisation in a subject in need thereof
to treat and prevent diseases and ailments involving angiogenesis, such as cardiovascular disease, myocardial or cerebral infarctions, mesenteric or limb ischaemia, wounds and vascular occlusion or stenosis
to accelerate wound healing, or the vascularisation of a skin graft, musculocutaneous flap or other surgically transplanted tissue, or to enhance the healing of surgically created anastomosis, and
to promote endothelial recovery after injury for example following angioplasty.

According to the present invention, vascular repair is enhanced by virtue of the therapeutic composition enhancing the ability of one or more cells that participate directly or indirectly in vascular repair and renewal to mobilise and/or to migrate, proliferate and form tubules or otherwise participate in vascular repair and/or angiogenic and/or neovascularisation and/or arteriogenic mechanisms in a subject. The methods of the invention are particularly relevant to subjects with low levels of circulating androgens and to aging subjects.

In a first aspect the present invention provides a method of promoting vascular repair in a subject in need thereof, the method comprising administering to the subject a composition comprising a therapeutically effective amount of an androgen receptor agonist, wherein said administration results in promoting vascular repair in the subject.

In one embodiment, the invention additionally or alternately includes one or both of (i) treating a cell to render it capable of participating in vascular repair or enhancing the ability of the cell to participate in vascular repair; and (ii) administering the cell alone or together with an androgen receptor agonist to the subject.

Accordingly in another aspect the present invention provides a method of promoting vascular repair in a subject in need thereof, the method comprising administering to the subject a therapeutically effective amount of a composition comprising a cell treated to render it capable of participating in vascular repair or enhancing the ability of the cell to participate in vascular repair, wherein said administration results in promoting vascular repair in the subject.

In another embodiment the method further involves isolating a cell capable of participating in vascular repair from a subject.

According to any of the preceding embodiments the composition for administration can also include one or more additional cells. The one or more additional cells can be treated or untreated cells.

Accordingly, the invention further includes one or both of (i) treating an additional cell to render it capable of participating in vascular repair or enhancing the ability of the cell to participate in vascular repair; and (ii) administering the additional cell to the subject.

The cell according to any of the forgoing embodiment can be for example any cell that is capable of being involved in vascular repair The cell is functional with respect to vascular repair so as to be capable of participating in one or more vascular repair processes, such as: 1) direct and/or indirect participation in angiogenesis, vasculogenesis and/or neovascularization; 2) direct and/or indirect participation in endothelial repair and regeneration and; 3) direct and/or indirect participation in end organ recovery and repair following ischaemia such as myocardial preservation and/or regeneration following myocardial infarction. The cell can be functional by virtue of being functional in nature, or by virtue of having been genetically-modified or genetically-repaired.

Examples of cells include for example endothelial progenitor cells, outgrowth endothelial cells, endothelial colony forming cells, bone marrow mononuclear cells, hemopoietic stem cells, erythroid progenitors and colon forming units, mesenchymal stem cells, cardiac stem cells, embryonic stem cells, any stem or progenitor cell capable of adopting a vascular cell lineage, pluripotent or progenitor cells induced from differentiated cells, side population cells, satellite cells, myoblasts, CD 34 positive and/or CD 133 positive and/or KDR positive cells, Stro bright and/or VCAM-1 positive cells, differentiated cells including endothelial cells, fibroblasts, monocytes, myocytes. etc.

In another aspect the present invention provides a method of promoting vascular repair in a subject in need thereof, the method comprising administering to a cell in vivo or ex vivo, an amount of a composition effective to activate, upregulate or stimulate or otherwise augment expression of an androgen receptor, thereby enhancing the ability of the cell to participate in vascular repair.

It will be understood that expression of an androgen receptor in a cell can be augmented in vivo or ex vivo. Ex vivo augmentation of the expression of an androgen receptor in a cell will require the administration of the cell to the subject. It will be understood that the augmented cell can optionally be co-administered with an androgen receptor agonist and/or a cell treated with an androgen receptor agonist.

In another aspect the invention provides a method of treatment or prophylaxis of one or more vascular diseases and/or vascular complications thereof in a subject in need thereof or in a subject at risk of developing such complications, said method comprising administering to the subject a therapeutically effective amount of an androgen receptor agonist, wherein said administration results in promoting vascular repair in the subject.

Accordingly this aspect of the invention additionally or alternately includes one or both of (i) treating a cell to render it capable of participating in vascular repair or enhancing the ability of the cell to participate in vascular repair; and (ii) administering the cell alone or together with an androgen receptor agonist to the subject.

Accordingly in another aspect the present invention provides a method of treatment or prophylaxis of one or more vascular diseases and/or vascular complications thereof in a subject in need thereof or in a subject at risk of developing such complications, said method comprising administering to the subject a therapeutically effective amount of a composition comprising a cell treated to render it capable of participating in vascular repair or enhancing the ability of the cell to participate in vascular repair, wherein said administration results in promoting vascular repair in the subject.

In another embodiment the method further involves isolating a cell capable of participating in vascular repair from a subject.

According to any of the preceding embodiments the composition for administration can also include one or more additional cells. The one or more additional cells can be treated or untreated cells.

Accordingly, the invention further includes one or both of (i) treating an additional cell to render it capable of participating in vascular repair or enhancing the ability of the cell to participate in vascular repair; and (ii) administering the additional cell to the subject.

The cell according to any of the forgoing embodiment can be for example any cell that is capable of being involved in vascular repair The cell is functional with respect to vascular repair so as to be capable of participating in one or more vascular repair processes, such as: 1) direct and/or indirect participation in angiogenesis, vasculogenesis and/or neovascularization; 2) direct and/or indirect participation in endothelial repair and regeneration and; 3) direct and/or indirect participation in end organ recovery and repair following ischaemia such as myocardial preservation and/or regeneration following myocardial infarction. The cell can be functional by virtue of being functional in nature, or by virtue of having been genetically-modified or genetically-repaired.

Examples of cells include for example endothelial progenitor cells, outgrowth endothelial cells, endothelial colony forming cells, bone marrow mononuclear cells, hemopoietic stem cells, erythroid progenitors and colon forming units, mesenchymal stem cells, cardiac stem cells, embryonic stem cells, any stem or progenitor cell capable of adopting a vascular cell lineage, pluripotent or progenitor cells induced from differentiated cells, side population cells, satellite cells, myoblasts, CD 34 positive and/or CD 133 positive and/or KDR positive cells, Stro bright and/or VCAM-1 positive cells, differentiated cells including endothelial cells, fibroblasts, monocytes, myocytes. etc Examples of complications, such as conditions or diseases that would benefit from said treatment include but are not limited to any condition associated with a narrowed or obstructed blood vessel, for example, narrowing of an artery, vein, or of a capillary system. Specific examples of such conditions or disease include but are not limited to coronary occlusive disease, carotid occlusive disease, arterial occlusive disease, peripheral arterial disease, atherosclerosis, myointimal hyperplasia (for example due to vascular surgery or balloon angioplasty or vascular stenting), thromboangiitis obliterans, thrombotic disorders, vasculitis, and the like.

Examples of conditions or diseases that can be prevented using the methods of the invention include, but are not necessarily limited to, heart attack (myocardial infarction) or other vascular death, stroke, death or loss of limbs associated with decreased blood flow, and the like.

Other forms of therapeutic methods include, but are not necessarily limited to, the use of an androgen to accelerate healing of wounds or ulcers; to improve the vascularisation of skin grafts or reattached limbs so as to preserve their function and viability; to improve the healing of surgical anastomoses (for example, as in re-connecting portions of the bowel after gastrointestinal surgery.)

In one embodiment of the invention the method relates to treating a subject that is androgen deficient. In one embodiment the subject is a male.

The present also provides a method of treatment or prophylaxis of a subject in need thereof, said method comprising:
(i) identifying a subject having one or more vascular diseases and/or vascular complications thereof or is at risk of developing one or more vascular diseases and/or vascular complications thereof and/or a subject in need of vascular repair or enhanced vascular repair
(ii) obtaining an amount of a composition comprising an androgen receptor agonist and/or a cell treated with an androgen receptor agonist and/or a cell treated to augment the expression of an androgen receptor; and
(iii) administering the composition to the identified subject in a therapeutic amount.

In an alternate embodiment the method provides alternatively or in addition to step (iii), a step of recommending administration of a composition comprising an androgen receptor agonist.

In another aspect the invention provides a method of treatment or prophylaxis comprising:
(i) identifying a subject having one or more vascular diseases and/or vascular complications thereof or is at risk of developing one or more vascular diseases and/or vascular complications thereof and/or a subject in need of vascular repair or enhanced vascular repair
(ii) obtaining an amount of a composition comprising an androgen receptor agonist and/or a cell treated with an androgen receptor agonist and/or a cell treated to augment the expression of an androgen receptor; and
(iii) formulating the composition at (ii) with a suitable carrier or excipient wherein said composition is in an amount to alleviate or prevent one or more vascular diseases and/or vascular complications thereof according to any embodiment herein in a subject in need thereof; and
(iv) administering said formulation to said subject.

In an alternate embodiment the method provides alternatively or in addition to step (iv), a step of recommending administration of a composition comprising an androgen receptor agonist.

In a particularly preferred embodiment, the method of the invention comprises repeated administration of a formulation comprising an androgen receptor agonist.

The present invention also provides a method for identifying an androgen receptor agonist, suitable for use in a formulation for the treatment or prophylaxis of one or vascular diseases and/or vascular complications thereof and/or for promoting vascular repair or enhancing vascular repair, said method comprising
(i) subjecting a cell to an amount of a candidate androgen receptor agonist in the presence and optionally in the absence of an androgen receptor antagonist and
(ii) detecting a parameter indicative of vascular repair and
(iii) selecting the candidate agonist that enhances vascular repair.

Parameters that are indicative of vascular repair include for example tubulogenesis, endothelial cell migration and endothelial cell migration.

In one embodiment, the parameter indicative of vascular repair is determined in an endothelial cell for example HUVEC or HCAEC, or a co-culture of fibroblasts and/ECs, or an EPC.

In one embodiment the method of identification involves
(i) subjecting a cell to an amount of a candidate agonist in the presence and optionally in the absence of an androgen receptor antagonist and
(ii) detecting migration of the cell, and
(iii) selecting a candidate agonist that enhances cell migration.

In one embodiment the cell is in a monolayer.

In a different embodiment the method of identifying an androgen receptor agonist comprises (i) subjecting a cell to an amount of a candidate agonist in the presence and optionally in the absence of an androgen receptor antagonist and
(ii) detecting cell numbers, and
(iii) selecting a candidate agonist that enhances cell numbers.

In another embodiment the method of identifying an androgen receptor agonist comprises
(i) subjecting a cell to an amount of a candidate agonist in the presence and optically in the absence of an androgen receptor agonist
(ii) detecting vascular network formation
(iii) selecting a candidate agonist that enhances vascular network formation.

In one embodiment the cell is in a co-culture of cells. Co-cultures can be assessed for example using immunohistochemistry for EC specific markers and image analysis software.

It is to be understood that all of the embodiments relating to the methods of treatment or prophylaxis and the methods promoting vascular repair in a subject in need thereof as described herein are applicable and relevant to this aspect.

The present invention clearly extends to the direct product of any method of identification or isolation of a compound or other composition of matter described herein.

It is to be understood that any compound of the present invention, identified or isolated compound or other composition of matter in substantially pure form, that is a compound or composition free from contaminants that might cause adverse side effects or contraindications or antagonise the activity of the active compound or other composition of matter, can be formulated into a medicament suitable for treatment according to the present invention.

Accordingly, in one example, the present invention further provides for the use of a compound or other composition of matter as described according to any embodiment herein, for the therapy or prophylaxis of one or more vascular diseases and/or vascular complications thereof in the manufacture of a medicament for the treatment of vascular diseases and/or vascular complications thereof and/or promotion of vascular repair.

In a preferred embodiment the compound or composition of matter is an androgen receptor agonist and/or a cell treated with an androgen receptor agonist and/or a cell treated to augment As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each embodiment described herein is to be applied mutatis mutandis to each and every other embodiment unless specifically stated otherwise.

Each embodiment describing a composition or compound or its use shall be taken to apply mutatis mutandis to a formulation comprising the composition or compound or its use unless the context requires otherwise or specifically stated otherwise.

Those skilled in the art will appreciate that the invention described herein is susceptible to variations and modifications other than those specifically described. It is to be understood that the invention includes all such variations and modifications. The invention also includes all of the steps, features compositions and compounds referred to or indicated in this specification, individually or collectively, and any and all combinations or any, two or more of said steps or features.

The present invention is not to be limited in scope by the specific embodiments described herein, which are intended for the purpose of exemplifcation only. Functionally-equivalent products, compositions and methods are clearly within the scope of the invention, as described herein.

DETAILED DESCRIPTION OF THE INVENTION

Androgen Receptor

Figure 1A:
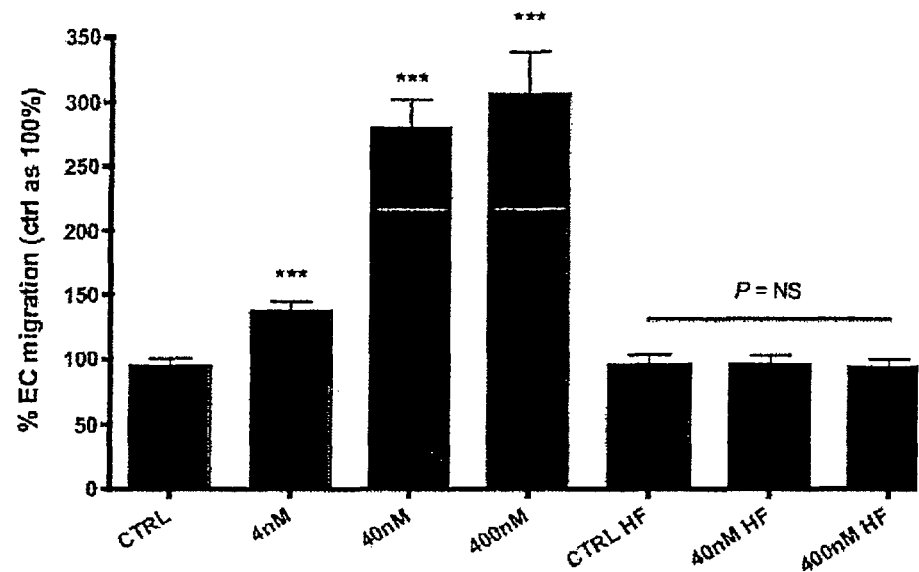
FIG. 1a. is a bar chart of effects of DHT on male EC migration.

The principal action of androgen is to regulate gene expression through the androgen receptor, which belongs to the superfamily of nuclear receptors. Nuclear receptors are ligand-inducible transcription factors that mediate the signals of a broad variety of fat-soluble hormones, including the steroid and vitamin D3 hormones, thyroid hormones retinoids he androgen receptor is activated by binding of androgenic hormones testosterone and dihydrotestosterone. The androgen receptor can modulate gene expression directly by interacting with specific elements in the regulatory regions of target genes or indirectly by activating various growth factor signalling pathways.

Androgens can act as chemical messengers in a wide range of species and target tissues to produce both slow genomic responses, and rapid non-genomic responses. Although it is clear that genomic responses to androgens are mediated by the formation of a complex of the hormone and its cognate steroid-hormone nuclear receptor, new evidence indicates that rapid responses are mediated by a variety of receptor types associated with the plasma membrane or its caveolae components, potentially including a membrane-associated nuclear receptor.

Androgen Receptor (AR) is differentially expressed on male and female cells. Furthermore, sex steroids may act in a gender-specific manner, with greater effects of estrogens and/or androgens in male or female cells (McCrohon J A, et al. "Androgen receptor expression is greater in macrophages from male than from female donors. A sex difference with implications for atherogenesis." Circulation 2000 Vol. 101 No. 3). As such, in light of the ability of androgens to promote vascular repair, modulation of AR expression in various tissues may augment said repair.

Various methods for the upregulation of AR expression will be known to those skilled in the art. These may include, prolonging the half life of AR, prevention of mechanisms of the degradation of AR, or overexpression of AR by transfection of cells or tissues with cDNA encoding AR (Lee, D. et al. "Expression and Degradation of Androgen Receptor: Mechanism and Clinical Implication" The Journal of Clinical Endocrinology & Metabolism Vol. 88, No. 9)

Androgen Receptor Agonists

As used herein the term "androgen receptor agonist" refers to any natural or synthetic compound, that binds to, and/or has an affinity for, and activates an androgen receptor. Androgen receptor agonists include full and partial agonists. Agonists can also be described as being androgenic. As exemplified herein the androgen receptor agonist is most preferably an androgen.

Naturally circulating androgenic steroids that are particularly useful in this invention are testosterone and 5α-dihydrotestosterone (DHT) and any derivatives thereof. In one embodiment the androgen receptor agonist is an ester derivative.

Other androgenic steroids that may demonstrate pro-angiogenic effects include, for example, boldenone, fluoxymesterone, mestanolone, mesterolone, methandrostenolone, 17-methyltestosterone, 17α-methyl-testosterone 3-cyclopentyl enol ether, norethandrolone, normethandrone, oxandrolone, oxymetholone, prasterone, stanlolone, stanozolol, and testosterone.

Other pro-angiogenic agents also include for example anabolic steroids such as androisoxazole, bolasterone, clostebol, ethylestrenol, formyldienolone, 4-hydroxy-19-nortestosterone, methenolone, methyltrienolone, nandrolone, okymesterone, quinbolone, stenbolone, trenbolone.

Physiological androgens, also include for example, Androstenedione, 4-hydroxy-Androstenedione, 11β-hydroxyandrostenedione, Androstanediol, Androsterone, Epi-androsterone, Adrenosterone, Dehydroepiandrosterone, Dehydroepiandrosterone Sulphate Testosterone, Epitestosterone, 5α-dihydrotestosterone, 5β-dihydrotestosterone, 11β-hydroxytestosterone and 11-ketotestosterone Additionally, non-steroidal androgen receptor agonists are also likely to exert pro-angiogenic effects. Non-steroidal agonists are described for example in US 2008/0057068.

Age Related Decline in Androgens—Androgen Deficiency

In one embodiment of the invention the subject has low levels of circulating androgens. In an alternate embodiment the subject has androgen levels within a normal range.

According to Wald et al (2006) "Testosterone replacement therapy for older men", *Journal of Andrology*, Vol. 27, No. 2, there is no agreement on the definition of hypogonadism in older men, and therefore a combination of clinical science and testosterone measurements is usually used as a tool to determine whether testosterone replacement therapy is indicated. The normal range of testosterone levels in young males is suggested to be valid for older men as well. The measurement of total blood testosterone is currently considered the most appropriate test to determine whether an older patient is hypogonadal or not. Some investigators have suggested that a total testosterone level of 200 mg/dL can appropriately be use as a cut-off value, below which an individual should be considered hypogonadal, regardless of age. However, the presence of hypogonadism is uncertain in patients whose total testosterone levels are in the border line range, between 200 and 300 mg/dL. Others consider individuals whose total testosterone levels are less than 300 mg/dL to be hypogonadal.

As used herein the term "androgen deficiency" is to be understood in its broadest sense to include any decline in circulating androgens in a subject. A decline in circulating androgens can be as a result of age or disease or trauma. It will be understood that according to the present invention a subject that is said to be androgen deficient can be fully or partially deficient and that a level of androgens that constitutes what is meant by partially deficient is subjective and dependent on the individual and their circumstances. The person skilled in the relevant art is capable of determining whether a subject is androgen deficient or not and whether the methods of the present invention are likely to be useful.

Dosage Rates

It will be understood that a person skilled is capable of appropriately determining a dosage rate of an androgen receptor agonist for the methods of administration as described herein. Dosage rates are dependent upon the route of administration and the vasculature, tissue or organ to be targeted and treated.

In the context of androgen deficiency, assuming that testosterone is being administered, a dosage regimen may include applying a dose of testosterone to the subject in an amount sufficient for the testosterone to reach the blood stream of the subject so as to achieve a serum concentration within a range between about 300 mg testosterone per dL serum to about 1000 mg testosterone per dL serum within at least about 24 hours of dosing of the androgen.

Supraphysiological testosterone is considered to be 40 nM. Trials conducted by others have involved weekly intramuscular administration of 250 mg testosterone enanthate, believed to affect supraphysiological concentrations of testosterone. Supraphysiological dosing regimens for testosterone enanthate involve weekly intramuscular injections ranging from 200-600 mg.

According to in vitro experiments performed by the inventors, the highest dose of DHT which is a more potent androgen than testosterone used was 400 nM. A number of studies have administered DHT for androgen therapy. Typically, administration is via a transdermal gel with doses ranging from 70-250 mg.

Administration of DHT however can result in the hormonal changes of increased plasma DHT together with negative feedback suppression of the pituitary-testicular axis (plasma total and free T, LH, FSH) see Ly L P, et al. "A double-blind, placebo-controlled, randomized clinical trial of transdermal dihydrotestosterone gel on muscular strength, mobility, and quality of life in older men with partial androgen deficiency." *J Clin Endocrinol Metab.* 2001; 86:40784088. Site specific or localised administration of DHT may be recommended.

Cells

The present invention encompasses cells in vivo and ex vivo capable of participating in vascular repair, enhancing vascular repair or preventing or reducing vascular disease or complication(s) thereof. The present invention encompasses the stimulation or treatment of cells in vivo or ex vivo to participate in migration, proliferation or tubulogenesis and/ or to facilitate other cells to perform these processes.

The cell is functional with respect to vascular repair so as to be capable of participating in one or more vascular repair processes, such as: 1) direct and/or indirect participation in angiogenesis, vasculogenesis and/or neovascularization; 2) direct and/or indirect participation in endothelial repair and regeneration and; 3) direct and/or indirect participation in end organ recovery and repair following ischaemia such as myocardial preservation and/or regeneration following myocardial infarction. The cell can be functional by virtue of being functional in nature, or by virtue of having been genetically-modified or genetically repaired.

Examples of cells include for example endothelial progenitor cells, outgrowth endothelial cells, endothelial colony forming cells, bone marrow mononuclear cells, haematopoietic stem cells, erythroid progenitors and colon forming units, mesenchymal stem cells, cardiac stem cells, embryonic stem cells, any stem or progenitor cell capable of adopting a vascular cell lineage, pluripotent or progenitor cells induced from differentiated cells, side population cells, satellite cells, myoblasts, CD 34 positive and/or CD 133 positive and/or KDR positive cells, Stro bright and/or VCAM-1 positive cells, differentiated cells including endothelial cells, fibroblasts, monocytes, myocytes. etc In one preferred embodiment a cell is of cardiovascular lineage or is capable of differentiating into a cell of said lineage.

Cells can be used in combination. For example the methods of the invention can involve infusion of different haematopoietic stem cell populations and ex vivo expanded and treated endothelial progenitor cells.

Cells (such as for example EPCs) can be isolated from a healthy subject and may be saved for use at a later date, and typically such cells are frozen under conditions that retains their viability. It will be appreciated that the cells may be obtained and enriched (expanded if necessary) before vascular complications arise or are apparent in a subject, and kept for immediate administration when necessary.

Alternatively, an cell is isolated from a subject in need of treatment.

A cell that has a capacity for repair can be isolated and/or treated, transformed and/or transfected prior to administration to a subject. Methods for isolating and/or administering such cells will be apparent to the skilled artisan and/or described herein.

For example, a natural source of EPCs includes bone marrow (e.g., with and without previous bleeding), peripheral blood (e.g., with and without enhancement from marrow), and peripheral blood mononuclear cells. Other sources are not to be excluded.

Cells may be isolated from such a source by any suitable method, typically involving cell fractionation and concentration.

A cell may be treated or rendered capable of participating in repair by being subjected to, contacted with, grown or otherwise cultured in the presence of an androgen receptor agonist. An androgen receptor agonist can for example be added to a growth medium for a cell. Alternatively a cell can be treated in the presence of a composition capable of activating, up regulating or otherwise augmenting the expression of an androgen receptor in said cell. In vitro treatment of cells are provided for example in Example 1. The scope of the invention is understood to include all methods of treatment or stimulation of a cell.

Pharmaceutical Compositions

As used herein, "pharmaceutical composition" means a "therapeutically effective amount" of the active ingredient, that is, the androgen receptor agonist, together with a pharmaceutically acceptable carrier or diluent. A "therapeutically effective amount" as used herein refers to that amount which provides a therapeutic effect for a given condition and administration regimen.

As used herein, the term "administering" refers to bringing a cell and/or subject in contact with a compound of the present invention. Administration is in vivo, i.e. in cells or tissues of living organisms, for example humans or ex vivo. In one embodiment, the present invention encompasses administering the compounds and compositions of the present invention to a subject.

Administrations

Pharmaceutical compositions containing the compounds of this invention can be administered to a subject by any method known to a person skilled in the art, such as orally, parenterally, intravascularly, paracancerally, transmucosally, transdermally, intramuscularly, intranasally, intravenously, intradermally, subcutaneously, sublingually, intraperitoneally, intraventricularly, intracranially, intravaginally, by inhalation, rectally, intratumorally, or by any means in which the androgen receptor agonist can be delivered to tissue (e.g., needle or catheter). Alternatively, topical administration may be desired for application to mucosal cells, for skin or ocular application. Another method of administration is via aspiration or aerosol formulation. Wald et al., (2006) (ibid) describes various routes of administration and dosage regimes. It is to be understood that Wald et al., relates to acute treatment and not vascular repair as described herein, and that the person skilled in the art such as for example a physician will know how to formulate, prescribe or administer an appropriate dosage of the compound for the methods of the present invention.

In one embodiment, the pharmaceutical compositions are administered orally, and are thus formulated in a form suitable for oral administration, that is as a solid or a liquid preparation. Suitable solid oral formulations include tablets, capsules, pills, granules, pellets, powders, and the like. Suitable liquid oral formulations include solutions, suspensions, dispersions, emulsions, oils and the like. In one embodiment of the present invention, the androgen receptor agonist is formulated in a capsule, for example a gelatine capsule. Oral testosterone undecanoate supplementation has been used in androgen therapy. In another embodiment the agonist can be formulated as sublingual formulations such as a cyclodextrin-complexed testosterone sublingual formulation.

Further, in another embodiment, the pharmaceutical compositions are administered by intravenous, intraarterial, or intramuscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intraarterially, and are thus formulated in a form suitable for intraarterial administration. In another embodiment, the pharmaceutical compositions are administered intramuscularly, and are thus formulated in a form suitable for intramuscular administration.

Intramuscular injection of long-acting esters, such as enanthate, is a traditional form of testosterone. Testosterone cypionate and testosterone proprionate are also considered here. Testosterone enanthate and cypionate have longer a longer action and have the same pharmacokinetic profile. They reach peak serum testosterone levels 24 hours after administration and decline gradually within 2 weeks.

In another embodiment an intramuscular dose of a biodegradable testosterone microsphere can be used (see Wald et al., (2006))

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of this invention or their physiologically tolerated derivatives such as salts, esters, N-oxides, and the like are prepared and applied as solutions, suspensions, or emulsions in a physiologically acceptable diluent with or without a pharmaceutical carrier.

Two types of transdermal patches are available, scrotal and nongenital and these are characterised by favourable pharmacokinetic behaviour and have proven to be an effective mode of delivery (Findlay J C, Place V, Snyder P J. "Treatment of primary hypogonadism in men by the transdermal administration of testosterone. *J Clin Endocrinol Metab.* 1989; 68:369-373). Daily use of the scrotal patch can produce midnormal serum testosterone levels in hypogonadal men 4 to 8 hours after application, and these levels gradually decrease over the next 24 hours Non-genital patches are known to provide midnormal serum levels 8 to 12 hours after the application of 2 nongenital patches. Transdermal testosterone gel (1% testosterone in a hydroalcoholic gel is also available. The skin serves as a reservoir for the sustained release of testosterone into the systemic circulation, allowing a single application of this formulation to provide continuous transdermal delivery of testosterone for 24 hours, producing circulating testosterone levels that approximate the normal levels (eg 300-1000 ng/dL) (Wald et al., ibid).

Further, in another embodiment, the pharmaceutical compositions are administered as a suppository, for example a rectal suppository or a urethral suppository.

Further, in another embodiment, the pharmaceutical compositions are administered by subcutaneous implantation of a pellet.

In a further embodiment, the pellet provides for controlled release of a compound over a period of time. A single intramuscular dose of a biodegradable testosterone microsphere formulation can provide normal testosterone levels in hypogonadal men for up to 11 weeks (see Wald et al., 2006). Formulations As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

Suitable excipients and carriers may be, according to embodiments of the invention, solid or liquid and the type is generally chosen based on the type of administration being used. Liposomes may also be used to deliver the composition. Examples of suitable solid carriers include lactose, sucrose, gelatin and agar. Oral dosage forms may contain suitable binders, lubricants, diluents, disintegrating agents, coloring agents, flavoring agents, flow-inducing agents, and melting agents. Liquid dosage forms may contain, for example, suitable solvents, preservatives, emulsifying agents, suspending agents, diluents, sweeteners, thickeners, and melting agents. Parenteral and intravenous forms should also include minerals and other materials to make them compatible with the type of injection or delivery system chosen. Of course, other excipients may also be used.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, cyclodextrins, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sobitan esters, stearic acids), antioxidants (e.g., ascorbic acid, sodium metabisulfite, butylated hydroxyanisole), stabilizers (e.g. hydroxypropyl cellulose, hydroxypropylmethyl cellulose), viscosity increasing agents (e.g. carbomer, colloidal silicon dioxide, ethyl cellulose, guar gum), sweetners (e.g. aspartame, citric acid), preservatives (e.g., Thimerosal, benzyl alcohol, parabens), coloring agents, lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates), and/or adjuvants.

In one embodiment, the pharmaceutical compositions provided herein are controlled release compositions, i.e. compositions in which the compound of this invention is released over a period of time after administration. Controlled or sustained release compositions include formulation in lipophilic depots (e.g. fatty acids, waxes, oils). In another embodiment, the composition is an immediate release composition, i.e. a composition in which all of the compound is released immediately after administration.

In yet another embodiment, the pharmaceutical composition can be delivered in a controlled release system. In yet another embodiment, a controlled release system can be placed in proximity to the therapeutic target, i.e., the heart, thus requiring only a fraction of the systemic dose (see, e.g., Goodson, in Medical Applications of Controlled Release, supra, vol. 2, pp. 116-138 (1984). Other controlled release systems are discussed in the review by Langer (Science 249:1627-1633 (1990).

The preparation of pharmaceutical compositions which contain an active component is well understood in the art, for example by mixing, granulating, or tablet-forming processes. The active therapeutic ingredient is often mixed with excipients which are pharmaceutically acceptable and compatible with the active ingredient. For oral administration, the compounds of this invention or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the compounds of this invention or their physiologically tolerated derivatives such as salts, esters, N-oxides, and the like are converted into a solution, suspension, or emulsion, if desired with the substances customary and suitable for this purpose, for example, solubilises or other.

Disease Therapy

Where appropriate disease therapy includes preventing, treating, suppressing, inhibiting or reducing the risk of, reducing the incidence of, ameliorating symptoms of, delaying progression of, or diminishing pathogenesis of a disease.

In some embodiments, the subject is human, while in other embodiments, the subject is non-human. In some embodiments, the subject is mammalian. In one embodiment, the subject is simian, bovine, feline, canine, ovine, porcine, equine, or murine.

In one embodiment, the subject is male, while in another embodiment, the subject is female. In one preferred embodiment the subject is an older male.

As used herein, the terms "prevention" and "treatment" shall not be taken to require an absolute i.e., 100% abrogation of impaired vascular function or vascular complication, or an absolute i.e., 100% prevention of the development of a vascular complication in a subject having risk factors therefor, and it is sufficient that there is a significant reduction in the adverse vascular effect(s) using the method of the present invention compared to the absence of prophylaxis or therapy in accordance with the present invention.

Similarly, the term "alleviating" or "alleviate" as used throughout this specification shall not be taken to require abrogation of impaired vascular function or vascular complication in a subject that is more than a significant effect compared to the absence of treatment in accordance with the present invention.

Similarly, the terms "inhibit", "enhance", "repress", "delay", "enhance", "induce", "activate" and "promote" as used throughout this specification shall not be taken to require any particular quantitative change, merely a modified level and/or activity and/or expression, or modified timing thereof, that is significant compared to the absence of treatment in accordance with the present invention.

Examples of the Invention

Example 1

In Vitro

Description of In Vitro Methods:

The effect of the non-aromatizable androgen dihydrotestosterone was assessed on three key angiogenic processes: endothelial cell (EC) migration, EC proliferation and EC tubulogenesis. Cells were treated with 0, 4, 40 or 400 nM dihydrotestosterone (DHT, a potent androgen) with and without the androgen-receptor antagonist hydroxyflutamide (HF).

(i) EC Migration

EC migration was assessed via a scratch assay and boyden chamber assay. Human Umbilical Endothelial Cells (HUVEC) monolayers were grown in the presence of varying doses of DHT±Hydroxyflutamide (HF), and either scratched or placed on top of permeable membranes. EC migration across the culture surface or through the membranes was assessed at 24 h and 6 h respectively via light and fluorescence microscopy respectively.

(ii) EC Proliferation

EC proliferation was assessed using two methods: direct counting of cell numbers and the MTS Assay. HUVECs were seeded at a density of 1×104 cells/ml (12 well plates for counting, 96 well plates for MTS assay) in endothelial growth media in the presence of varying doses DHT±Hydroxyflutamide (HF). After 48 h, cells were either harvested from 12 well plates and counted or incubated with MTS reagent in the 96 well plates with absorbance measured subsequently at 490 nm measured.

(iii) EC Tubulogenesis

Vascular network formation by HUVECs was assessed using a previously described co-culture assay of fibroblasts and ECs (Sieveking, D. et al J Am Coll Cardiol 2008; 51:660-8). Co-cultures were grown in the presence of DHT±Hydroxyflutamide (HF). After 72 h, co-cultures were assessed using immunohistochemistry for EC specific markers and image analysis software.

Description of In Vitro Results:

(i) Endothelial Cell (EC) Migration

Figure 1B:
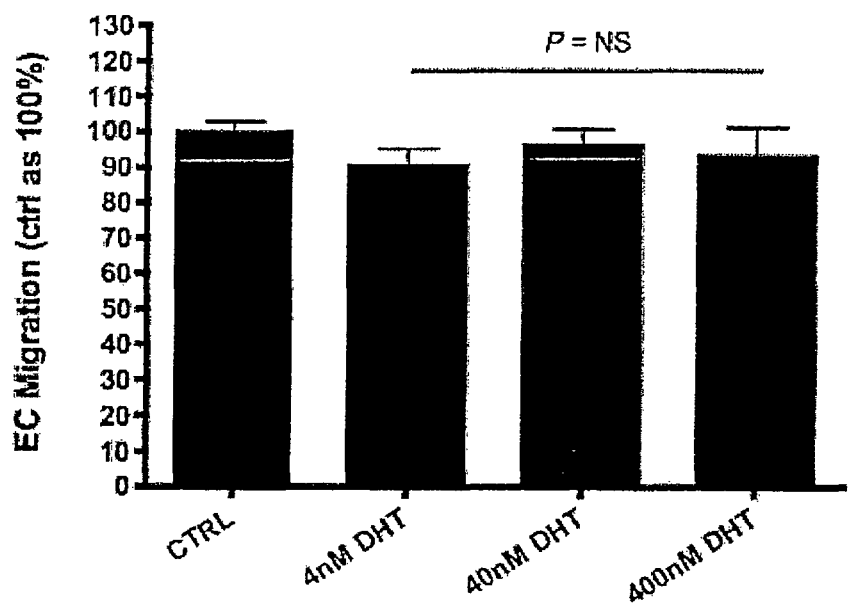
FIG. 1b. is a bar chart of effects of DHT on female EC migration.

DHT administration induced dose-dependent male EC migration after 24 h (138±7%, 280±23% and 306±32% vs. 100% control value for DHT at 4, 40, and 400 nM, respectively, $P<0.01$, ANOVA). Addition of the androgen receptor antagonist HF abrogated DHT mediated EC migration (96±6% and 94±6% vs. 100% control value for 40 nM DHT+HF and 400 nM+HF respectively, $P>0.05$) (FIG. 1a). DHT did not augment EC migration in female donor cells (90±5%, 96±5% and 93±8% vs. 100% control value for DHT at 4, 40, and 400 nM, respectively, $P>0.05$, ANOVA) (FIG. 1b).

(ii) EC Proliferation

Figure 2A:
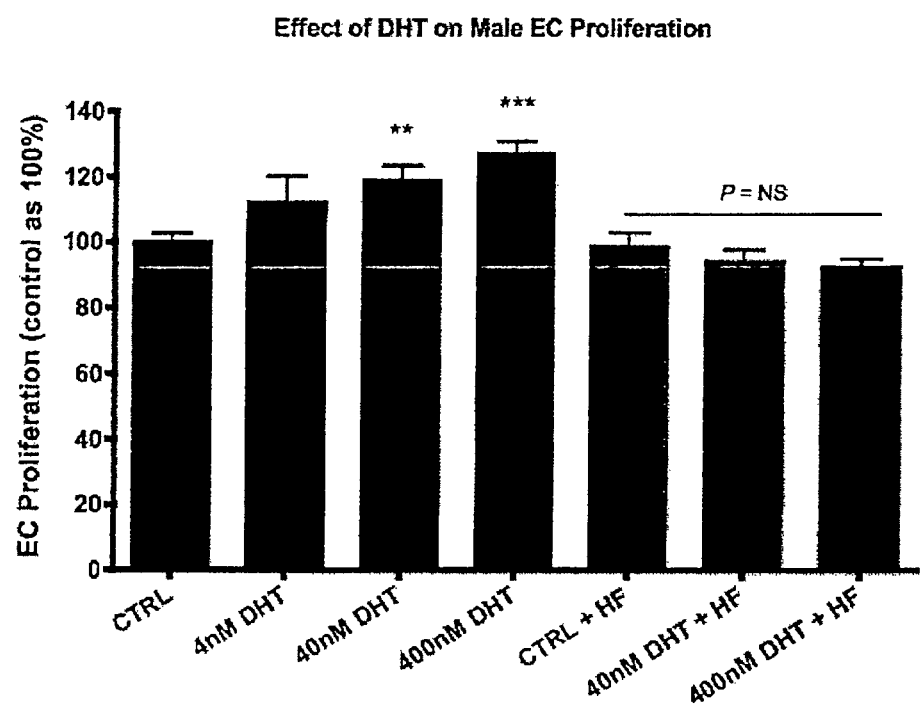
FIG. 2a. is a bar chart of effects of DHT on male EC proliferation.
Figure 2B:
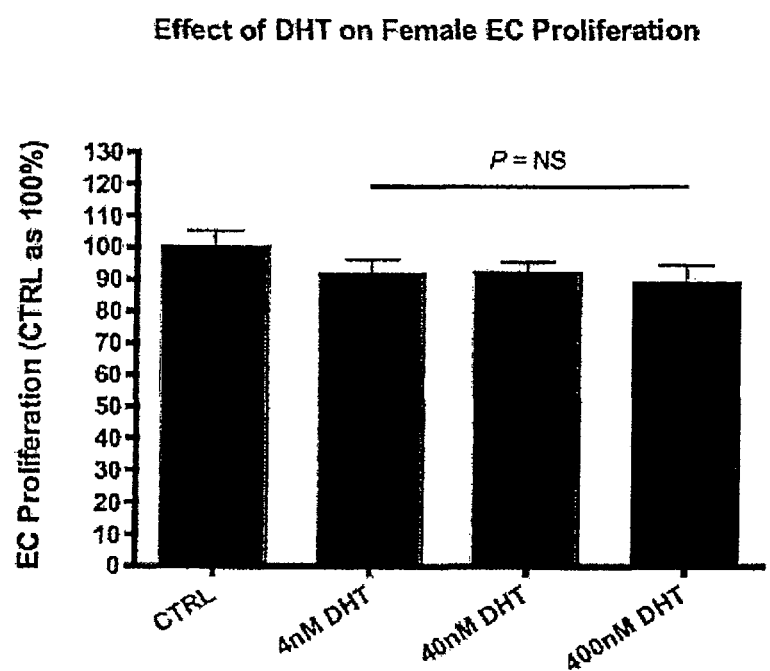
FIG. 2b. is a bar chart of effects of DHT on female EC proliferation.

DHT induced a dose-related increase in proliferation after 48 h (112±8%, 118±5% and 127±4% vs. 100% control value for DHT at 4, 40, and 400 nM, respectively, $P<0.001$, ANOVA). Addition of the androgen receptor antagonist HF abrogated DHT mediated EC proliferation (94±4% and 93±3% vs. 100% control value for 40 nM DHT+HF and 400 nM+HF respectively, $P>0.05$) (FIG. 2a). DHT did not augment EC proliferation in female donor cells (92±5%, 92±3% and 89±6% vs. 100% control value for DHT at 4, 40, and 400 nM, respectively, $P>0.05$, ANOVA) (FIG. 2b).

(iii) EC Tubulogenesis

Figure 3A:
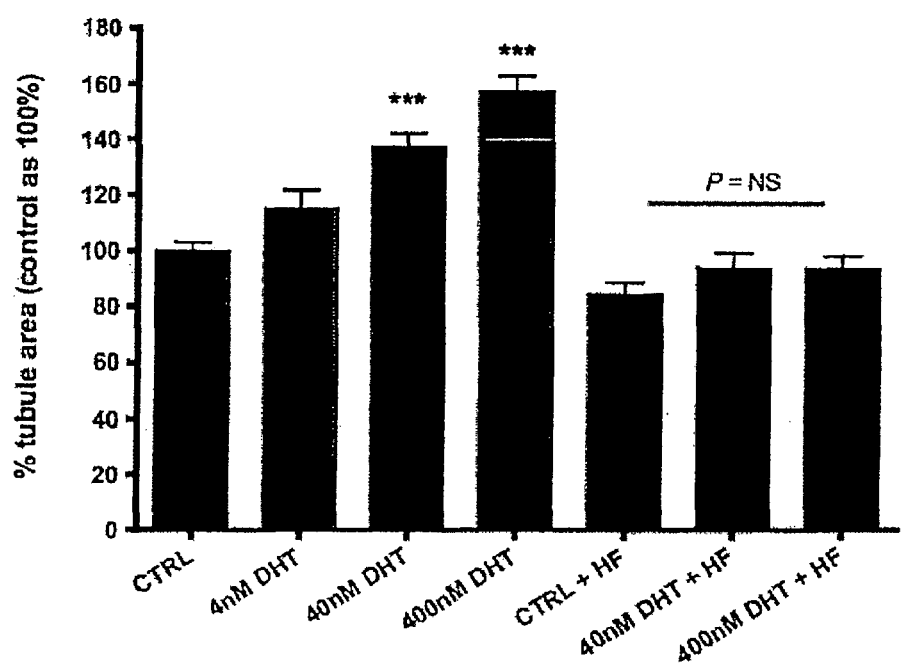
FIG. 3a. is a bar chart of effects of DHT on male EC tubulogenesis.
Figure 3B:
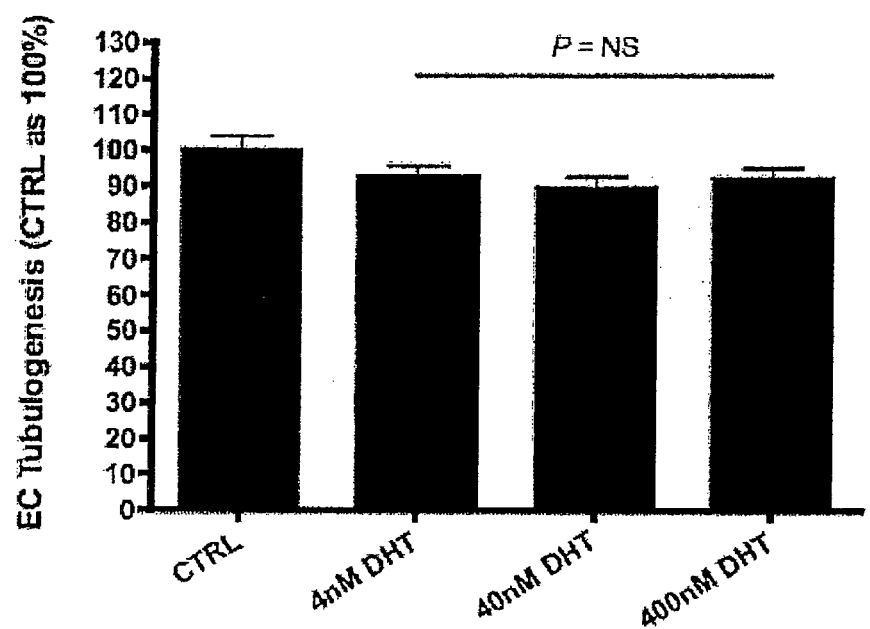
FIG. 3b. is a bar chart of effects of DHT on female EC tubulogenesis.

Chronic exposure to DHT also increased tubule formation (115±7%, 137±5% and 157±6% vs. 100% control value for DHT at 4, 40, and 400 nM, respectively, $P<0.001$, ANOVA). Addition of the androgen receptor antagonist HF abrogated DHT mediated EC tubulogenesis (94±4% and 93±3% vs. 100% control value for 40 nM DHT+HF and 400 nM+HF respectively, $P>0.05$) (FIG. 3a). DHT did not augment EC tubulogenesis in female donor cells (92±3%, 90±3% and 92±3% vs. 100% control value for DHT at 4, 40, and 400 nM, respectively, $P>0.05$, ANOVA) (FIG. 3b).

Example 2

In Vivo

Description of Mouse Models Used

Animals

Male C57B16/J mice were either castrated or sham-castrated after reaching sexual maturity (6 weeks). After a period of 10 days, 50% of both castrated and sham-castrated mice received a 1 cm subcutaneous silastic implant containing DHT.

(i) Matrigel Plug Implantation Model

Commercially available Matrigel (BD biosciences) without Phenol Red was supplemented with bFGF (100 ng/mL) and implanted subcutaneously (250 (1) in male mice. After a period of fourteen days, Matrigel plugs were removed from the mice and assessed for vascularization using standard immunohistochemical techniques. This model and method is described in detail in Passaniti A, et al. A simple, quantitative method for assessing angiogenesis and antiangiogenic agents using reconstituted basement membrane, heparin, and fibroblast growth factor. *Lab Invest.* 1992; 67:519-528.

(ii) Hindlimb Ischaemia Model

Complete femoral artery excision from the left hind limb of male mice was performed using an operative procedure developed in the laboratory of the late Dr. Jeffrey Isner, which was modified to include disruption of the subcutaneous branch in the medial thigh. Perfusion of the hindlimbs was measured by laser Doppler perfusion imaging (LDPI; Moor Instruments) which utilises a near-infrared laser diode to measure subcutaneous blood flow as a function of light scattering by moving red blood cells (Doppler shift). This technique allows for repeated, non-invasive, quantitative measurements of tissue perfusion that are expressed as the ratio of signal in the ischemic and contralateral non-ischemic hind limb. Perioperative LDPI provides a method of demonstrating successful surgical outcome (i.e. presence of critical limb ischaemia). The serial changes in perfusion that are observed following femoral artery excision and revascularization have been shown to correlate with changes in vessel density as determined by histological analysis (Couffinhal T, et al. Mouse model of angiogenesis. *Am J Pathol.* 1998; 152:1667-1679.).

In addition to the quantitative analysis of perfusion in the foot by LDPI, the animals were clinically evaluated and scored for physical evidence of ischemic tissue damage and impairment of motor function.

(iii) Angiogenic Cell Mobilization

Mononuclear cells were harvested from the spleens and bone marrow of all animals and assessed via cell culture and flow cytometry. Cells were and stained with fluorescein isothiocyanate-lectin and/or 1,1(-dioctadecyl-3,3,3(,3(-tetramethylindocarbocyanine (DiI)-labelled, acetylated low-density lipoprotein (Vasa M, et al. Number and migratory activity of circulating endothelial progenitor cells inversely correlate with risk factors for coronary artery disease. *Circ Res.* 2001; 89:e1-e7).

The animal models are both well established for the in vivo assessment of angiogenesis in the presence (Hindlimb Ischaemia) or absence (Matrigel plug) of an ischemic stimulus.

Detailed Description of In Vivo Results:

(i) Matrigel Plug Implantation Model

Figure 4:
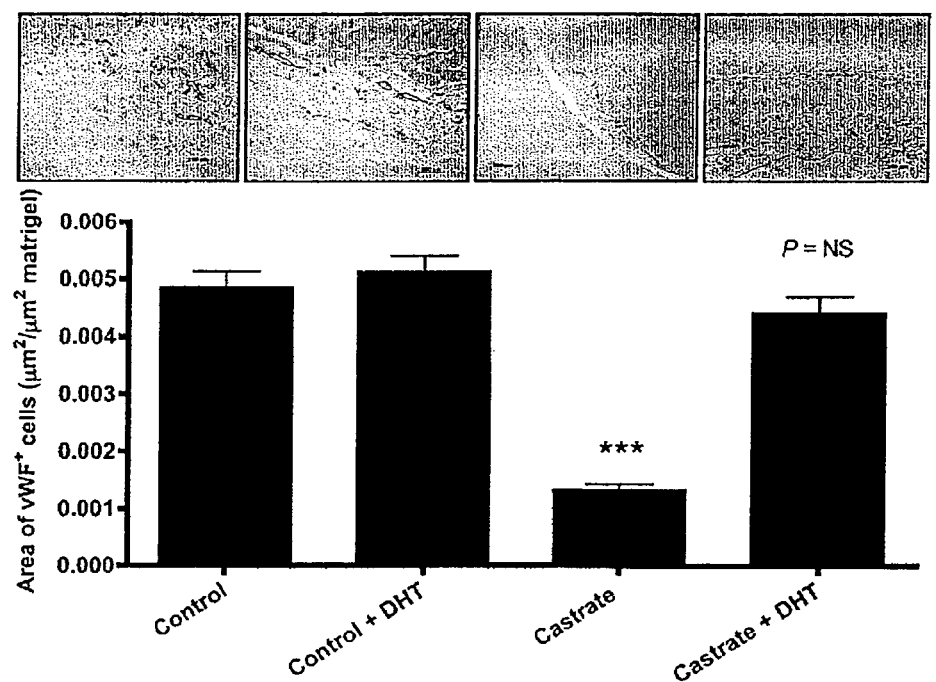
FIG. 4. depicts effects of Castration and DHT Treatment on Angiogenesis in Male Mice. Castrated and sham-castrated mice with and without DHT treatment were implanted with matrigel plugs. After 14 days, plugs were excised and immunohistochemically stained for the endothelial cell specific antigen von Willebrand Factor (vWF).

Male castration markedly decreased in vivo vascularization of Matrigel plugs (4.8±0.2×10-3 vs. 1.3±0.1×10-3 (m2 vWF+ cells/(m2 matrigel for control vs. castrated mice, $P<0.0001$). Androgen replacement reversed castration-effects on angiogenesis (4.3±0.3×10-3 (m2 vWF+ cells/(m2, $P<0.001$ vs. castrated mice)(FIG. 4).

(ii) Hindlimb Ischaemia Model

Male castration markedly inhibited the rate of recovery from hindlimb ischaemia (Laser Doppler Perfusion Index (LDPI) ischemic/non-ischemic ratio after 11 days, control: 0.54±0.04, castrate: 0.39±0.04, $P<0.05$). Androgen replacement not only reversed castration-effects, but also accelerated recovery in hindlimb ischaemia (LDPI after 7 days, control: 0.39±0.03, castrate+DHT: 0.6±0.06, $P<0.01$) (FIG.

Figure 5A:
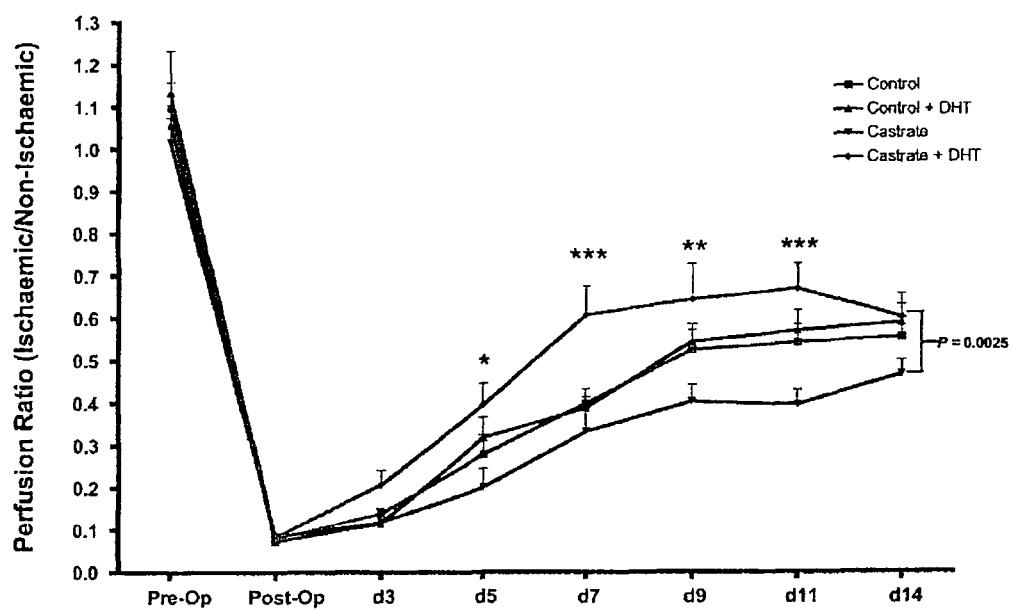
FIG. 5a. depicts effect of Castration and DHT treatment on the recovery of mice subjected to femoral artery ligation. Limb perfusion ratio. For each group of mice, the mean (±SEM) ratio of perfusion in the ischemic-non-ischemic limb at the indicated times was determined by LDPI. Differences between groups were assessed by 2-way ANOVA with Bonferroni correction (brackets at right); *P<0.05, P<0.01, *P<0.001 comparisons between castrate and castrate+DHT at individual time point.
Figure 5B:
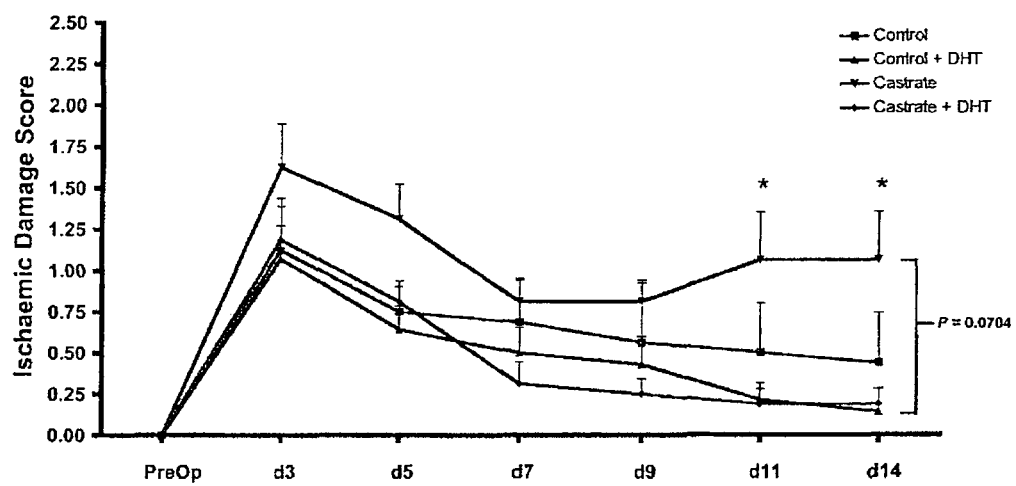
FIG. 5b. depicts effect of Castration and DHT treatment on the recovery of mice subjected to femoral artery ligation. Tissue damage score. Mice were scored as follows: 0, no tissue damage; 1, mild discoloration; 2, moderate discolouration; 3, Tissue loss/necrosis; 4, loss of foot or more. The mean score (±SEM) was determined at each time point. Differences between groups were assessed by 2-way ANOVA with Bonferroni correction (brackets at right), *P<0.05, comparisons between castrate and castrate+DHT at individual time point.
Figure 5C:
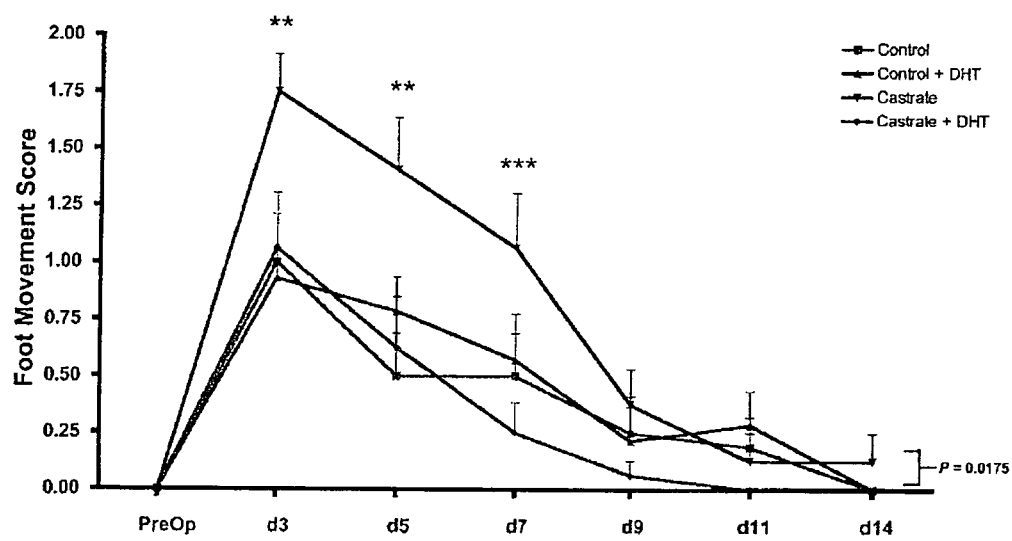
FIG. 5c. depicts effects of Castration and DHT treatment on the recovery of mice subjected to femoral artery ligation. Foot Movement Score. Mice were scored as follows: 0, normal response (plantar/toe flexion in response to tail traction); 1, plantar but not toe flexion; 2, no plantar or toe flexion; 3, dragging of foot. The mean score (±SEM) was determined at each time point. Differences between groups were assessed by 2-way ANOVA with Bonferroni correction (brackets at right), P<0.01, *P<0.001 comparisons between castrate and castrate+DHT at individual time point.

5a). These results were also mirrored in clinical evaluations of ischemic damage and motor function (FIGS. 5b and c respectively).

These findings suggest that androgens participate in modulation of cardiovascular regeneration with particular implications for the role of androgen replacement in men.

(iii) Angiogenic Cell Mobilization

Figure 6A:
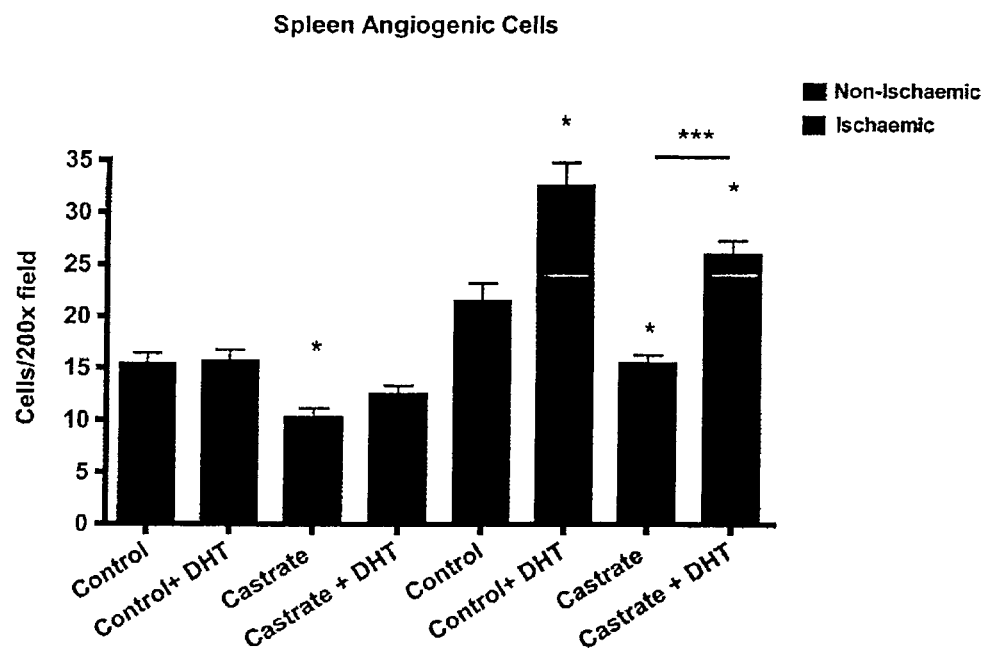
FIG. 6a. is a bar chart of effects of Castration and DHT Treatment on Mobilization of Spleen Angiogenic cells. MNCs were isolated from the spleens of mice and cultured in endothelial growth medium, and the mean (±SEM) number (per ×200 field) of angiogenic cells was determined. *P<0.05 compared with respective control.
Figure 6B:
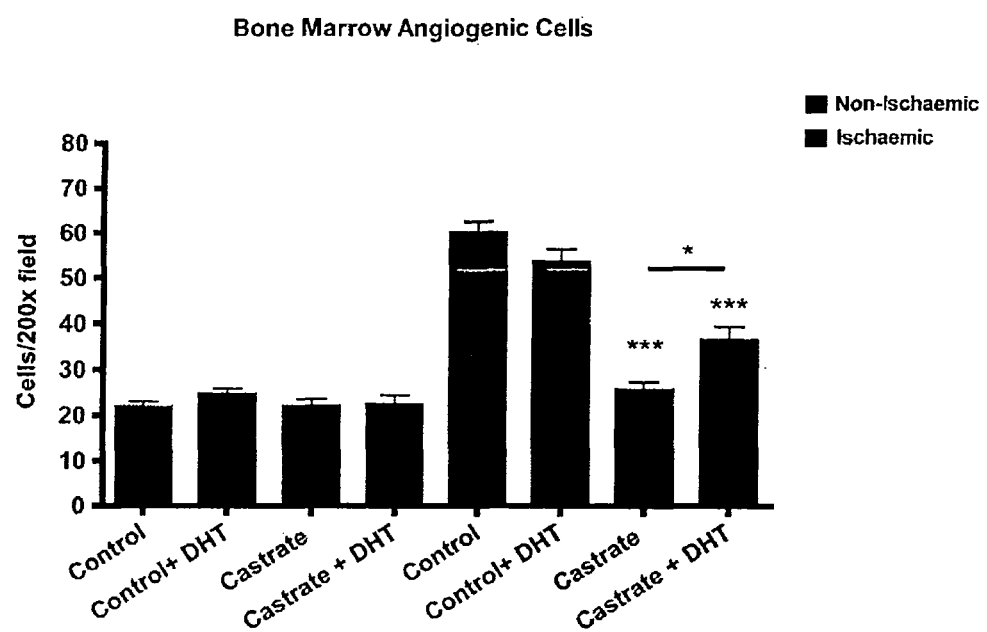
FIG. 6b. is a bar chart of effects of Castration and DHT Treatment on Mobilization of Bone Marrow Angiogenic cells. MNCs were isolated from the bone marrow of mice and cultured in endothelial growth medium, and the mean (±SEM) number (per ×200 field) of angiogenic cells was determined. *P<0.05 compared with respective control.

To test the hypothesis that the observed differences in angiogenic responses were associated with differences in mobilization of angiogenic cells, MNCs were isolated from mice used in both animal models outlined above. MNCs, were harvested from both the spleen, which serves as a reservoir of circulating cells, and the bone marrow. Castration of male mice markedly decreased angiogenic cells detected in the spleens of mice, both in the presence (22±1.7 vs. 16±0.8 Angiogenic cells/×200 field for control vs. castrated mice, $P<0.05$) and absence (15.4±1 vs. 10.3±0.9 Angiogenic cells/×200 field for control vs. castrated mice, $P<0.05$) of an ischemic stimulus (FIG. 6a). In the absence of ischaemia DHT treatment reversed castration effects on angiogenic cell mobilisation (10±0.9 Angiogenic cells/×200 field for castrate+DHT $P>0.05$ vs. control). Indeed, in the presence of ischaemia, not only was angiogenic cell mobilization normalized, but augmented (26±1.3 Angiogenic cells/×200 field for castrate+DHT $P<0.05$ vs. respective control). In the bone marrow, castration dramatically reduced the numbers of angiogenic cells in the presence of ischaemia, a finding which was reversed by DHT treatment (Control: 60±2.4, Castrate: 26±1.7, castrate+DHT: 36±3 Angiogenic cells/×200 field, $P<0.001$ for castrate and castrate+DHT vs. control, $P<0.05$ for castrate vs. castrate+DHT) (FIG. 6b).

Together, these in vivo findings suggest that androgens participate in modulation of cardiovascular regeneration with particular implications for the role of androgen replacement in men.

Example 3

Human Studies

Effects of Exogenous Androgen Administration on Endothelial Progenitor Cell Mobilisation and Function in Men Rationale: Androgens are known to stimulate erythropoiesis and haematopoietic stem cell proliferation by direct effects and also via stimulation of EPO production. Recent evidence suggests that EPO is a potent stimulus for EPC mobilisation and ischaemia-induced angiogenesis. We will evaluate the effects of androgen replacement in on EPC mobilisation and function in elderly men with partial androgen deficiency.

Prospective Evaluation of Androgen Effects on EPC Mobilization and Function in a Randomised Placebo-Controlled Trial Involving Elderly Men with Partial Androgen Deficiency.

Patient Recruitment:

Healthy, ambulatory men over the age>60 years with partial androgen deficiency (n=40), defined as the presence on 2 occasions of low serum total testosterone (<15 nmol/L) will be randomised to 3 months treatment with intramuscular testosterone injection (100 mg fortnightly, Sustanon, Organon Laboratories) or placebo. The patients will be enrolled via an ongoing collaboration with AI2 and the Andrology Clinic at Concord Hospital, Sydney. Men will be excluded from the study if they have prostatic disease requiring medical or surgical treatment or have chronic medical diseases or medications likely to interfere with safe participation in androgen therapy. Full medical history including cardiovascular risk factors and clinical examination will be undertaken on all patients.

Blood Collection, Biochemical Markers, Hormone Assays and Monocyte Isolation:

Fasting morning blood samples will be obtained at weeks: 0, 1, 6 and 14 of the trial. Serum T, DHT and oestradiol will be measured at 0, 6 and 14 weeks by standard methods. In addition lipid profile, fibrinolytic markers, prostatic specific antigen and full blood count including haemoglobin will be measured by the Royal Prince Hospital Pathology. Serum EPO and VEGF will be measured by ELISA. For EPC studies a 20 ml blood sample will be collected and buffered with sodium citrate. Mononuclear cells will be isolated with the use of a Ficoll density gradient (Biocoll, Biochrom) according to standard protocols.

Quantitation of EPCs:

EPCs and early haematopoietic stem cells will be quantitated by FACS analysis (Beckman Coulter FC 500 at HRI) for CD34+/KDR+ and CD34+/CD133+ cells, respectively. Mononuclear cells will be resuspended in 100 "l of a FACS buffer containing phosphate-buffered saline, 0.1% bovine albumin, and aprotinin (20"l/mL). Immunofluorescent cell staining will be performed with the use of the fluorescent conjugated antibodies to CD34-fluorescein isothiocyanate (FITC) (Becton Dickinson) in combination with KDR (R&D Systems) or CD133-phycoerythrin (Miltenyi). For the identification of KDR+ cells, indirect immunolabeling will be performed with the use of a biotinylated goat mononuclear antibody against the extracellular domain of human KDR (R&D Systems). IgG2a-FITC-PE antibody (Becton Dickinson) will be used as a negative control. Cell fluorescence will measured immediately after staining.

To assess the reproducibility of the measurements, two separate blood samples will be obtained, on day 0 from 5 subjects. The intraclass correlation between the two probes will be computed.

EPC Colony Forming Unit (CFU) Assay:

In endothelial basal medium (CellSystems) with supplements, 1×107 mononuclear cells will be seeded on human fibronectin-coated plates (Sigma-Aldrich). After 48 hours, 1×106 nonadherent cells will be transferred into new fibronectin-coated wells to avoid contamination with mature endothelial cells and nonprogenitor cells. After seven days, endothelial CFUs in at least 3 wells will be counted by two observers blinded to the subject's treatment. Confirmation of endothelial-cell lineage will be performed by immunostaining for KDR and CD31.

Reverse Transcription Polymerase Chain Reaction (RT-PCR):

EPC expression of AR, VEGF, VEGF receptors (1, 2 and VEGF 165 1 and 2) will be assessed by RT-PCR (11).

Effects of DHT and T on EPC Proliferation and EPC-mediated Tubulogenesis in vitro: will be evaluated using the EC proliferation and fibroblast co-culture assays as outlined in 1.3 and 1.4.

Statistical Analysis:

We calculated that for men receiving ART, 40 participants would be needed to detect a 30% increase in EPCs in a randomised study with 80% power and 5% significance.

Anticipated Results and Further Studies:

Given that T stimulates haematopoietic stem cell proliferation, we anticipate that T replacement will stimulate both EPC and early haematopoietic progenitor cell mobilisation. Functional assays will assess the in vitro effects of androgens on EPC proliferation and tube formation. Future studies may evaluate these effects of testosterone in the context of men with CAD, by evaluating both EPC mobilisation and myocardial perfusion endpoints.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

The invention claimed is:

1. A method of promoting or enhancing vascular repair in a male subject who is suffering from a vascular blockage, wherein the method comprises administering to the subject a composition comprising a therapeutically effective amount of an androgen receptor agonist so that the subject is chronically exposed to the androgen receptor agonist, and wherein the composition is administered in an amount sufficient to stimulate angiogenesis, neovascularization and/or vascular regeneration in the subject to thereby promote or enhance vascular repair in the subject, wherein the vascular blockage is a result of critical limb ischaemia or thromboangiitis obliterans.

2. The method of claim 1, wherein the androgen receptor agonist is an androgen.

3. The method of claim 1, wherein the androgen receptor agonist is a steroidal androgen.

4. The method of claim 1, wherein the androgen receptor agonist is testosterone.

5. The method of claim 1, wherein the subject is androgen deficient.

6. The method of claim 1, wherein the subject is not androgen deficient.

7. The method of claim 1, wherein the androgen receptor agonist is dihydrotestosterone (DHT).

8. The method of claim 1, wherein the androgen receptor agonist is dehydroepiandrosterone (DHEA), androsterone, epitestosterone, androstenedione, dehydroepiandrosterone, or androstanediol.

9. The method of claim 1, comprising administering to the subject a plurality of dosages of the composition.

10. The method of claim 1, comprising administering the composition to the subject daily, weekly or fortnightly.

11. The method of claim 1, comprising detecting the presence of one or more indicator of vascular repair in the subject after administration of the composition to the subject.

12. The method of claim 11, wherein the one or more indicator of vascular repair is one or more of the group consisting of tubulogenesis, endothelial cell migration, and endothelial cell proliferation.

13. The method of claim 1, comprising selecting a subject who is suffering from critical limb ischaemia or thromboangiitis obliterans as a subject suitable for administration of the composition.

14. A method of promoting or enhancing vascular repair in a male subject who is suffering from critical limb ischaemia, wherein the method comprises administering to the subject a composition comprising a therapeutically effective amount of an androgen receptor agonist so that the subject is chronically exposed to the androgen receptor agonist, and wherein the composition is administered in an amount sufficient to stimulate angiogenesis, neovascularization and/or vascular regeneration to thereby promote or enhance vascular repair in the subject.

15. A method of promoting or enhancing vascular repair in a male subject who is suffering from thromboangiitis obliterans, wherein the method comprises administering to the subject a composition comprising a therapeutically effective amount of an androgen receptor agonist so that the subject is chronically exposed to the androgen receptor agonist, and wherein the composition is administered in an amount sufficient to stimulate angiogenesis, neovascularization and/or vascular regeneration to thereby promote or enhance vascular repair in the subject.

* * * * *